US010376410B2

(12) United States Patent
Flanagan

(10) Patent No.: US 10,376,410 B2
(45) Date of Patent: Aug. 13, 2019

(54) AUTOMATED, SNORE ACTIVATED ELECTRO-MECHANICAL MANDIBULAR ADVANCEMENT DEVICE

(71) Applicant: Craig Flanagan, Wall, NJ (US)

(72) Inventor: Craig Flanagan, Wall, NJ (US)

( * ) Notice: Subject to any disclaimer, the term of this patent is extended or adjusted under 35 U.S.C. 154(b) by 446 days.

(21) Appl. No.: 15/148,517

(22) Filed: May 6, 2016

(65) Prior Publication Data

US 2016/0324681 A1    Nov. 10, 2016

Related U.S. Application Data

(60) Provisional application No. 62/230,438, filed on Jun. 5, 2015, provisional application No. 62/179,473, filed on May 8, 2015.

(51) Int. Cl.
*A61B 5/00* (2006.01)
*A61B 5/08* (2006.01)
*A61F 5/56* (2006.01)

(52) U.S. Cl.
CPC ............... *A61F 5/566* (2013.01); *A61B 5/08* (2013.01); *A61B 5/4818* (2013.01); *A61B 5/4833* (2013.01); *A61B 5/4836* (2013.01); *A61B 5/682* (2013.01)

(58) Field of Classification Search
CPC ...... A61F 5/566; A61F 5/56; A61F 2005/563; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004; A61N 2/006; A61N 2/008; A61N 1/40; G09B 19/003; G09B 23/28; Y10T 29/49826; A61C 7/08; A61C 19/063
See application file for complete search history.

(56) References Cited

U.S. PATENT DOCUMENTS

2015/0305671 A1*   10/2015   Yoon .................. A61B 5/01
                                                                          600/301

* cited by examiner

*Primary Examiner* — Tarla R Patel
(74) *Attorney, Agent, or Firm* — Boag I Law, PLLC

(57) ABSTRACT

An automated mandibular advancement device (MAD) is described for the treatment of sleep disorders involving the occlusion of upper airway gas flow during sleep; one example being obstructive sleep apnea. In embodiments, a MAD projects the lower jaw forward only after the patient has fallen asleep. Embodiments of the may track patient sleep parameters for later review by the patient and/or the treating physician to assess the quality of sleep and efficacy of the treatment regime. An actuator placed laterally within a band allows the integral microprocessor to actuate the lower jaw tray forward upon sensing of snoring activity (or upon exceeding a pre-set timer threshold).

5 Claims, 10 Drawing Sheets

106 ←

Snoring Sound Signal Processing Technique

Raw Sound Signal

108 ←

Sound Signal after Digital Filtering (e.g. bandpass filter)

110 ←

Signal Then Rectified and Smoothed

112 ←

Signal Then Integrated and compared to Snoring Threshold

Actuate the Linear Actuator to deploy the lower jaw extension

AUTOMATED, SNORE ACTIVATED ELECTRO-MECHANICAL MANDIBULAR ADVANCEMENT DEVICE

PRIORITY CLAIM

This application claims priority to U.S. Patent Application Nos. 62/179,473, filed May 8, 2015, and 62/230,438, filed Jun. 5, 2015, each titled AN AUTOMATED, SNORE ACTIVATED ELECTRO-MECHANICAL MANDIBULAR ADVANCEMENT DEVICE, the contents of which are incorporated by reference in its entirety.

BRIEF DESCRIPTION OF THE DRAWINGS

The features and advantages of the present disclosure will be more fully understood with reference to the following detailed description when taken in conjunction with the accompanying figures, wherein.

SUMMARY

Figure 1:
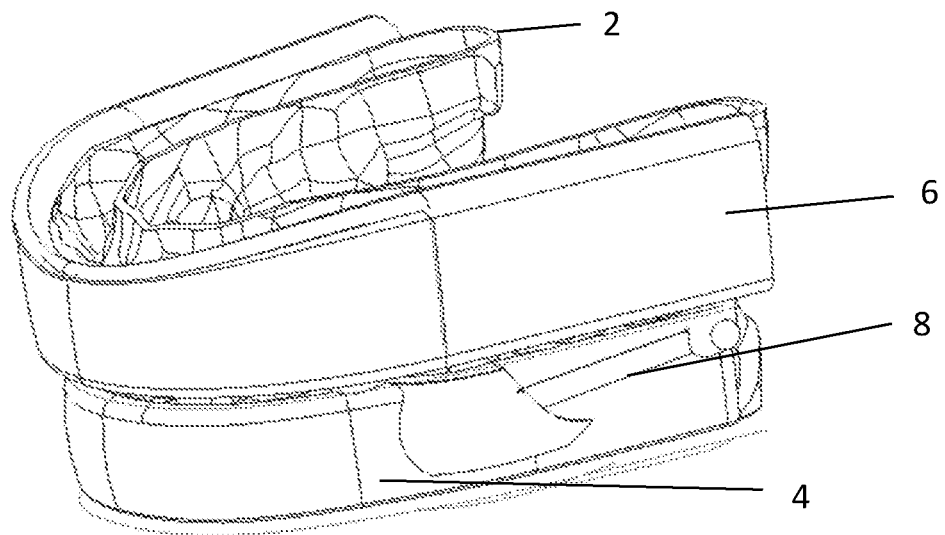
FIG. 1 depicts an embodiment of the invention as completely assembled as during use.
Figure 2:
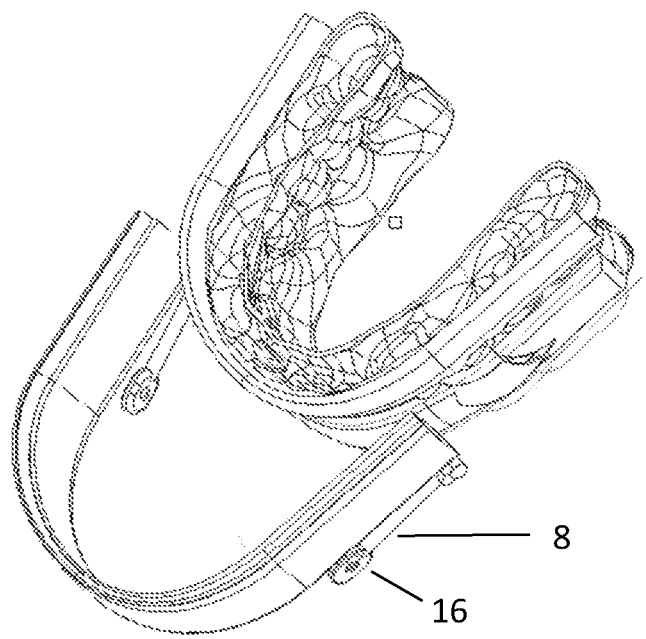
FIG. 2 depicts an embodiment of the invention with the actuator-containing band detached from the upper jaw tray.
Figure 3:
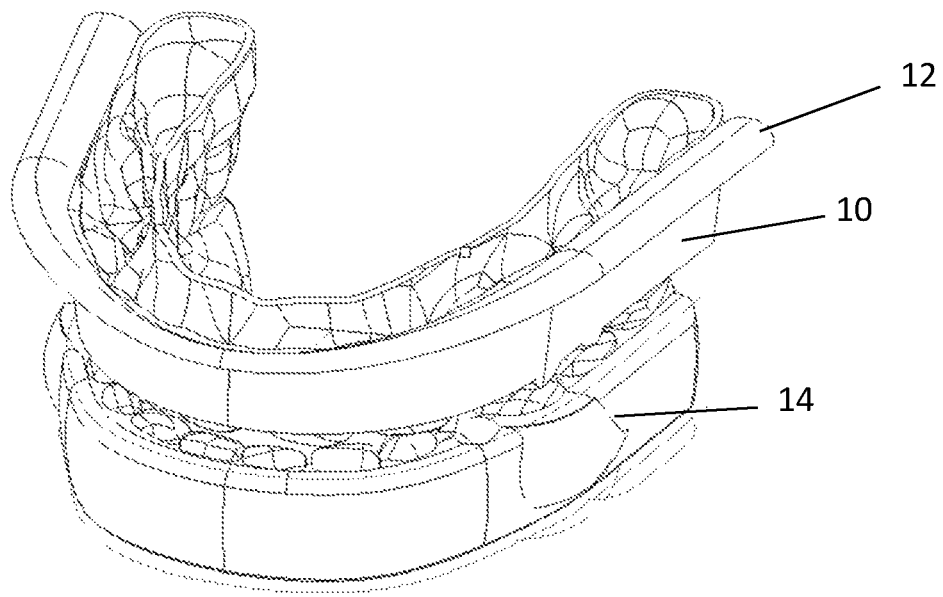
FIG. 3 depicts the upper and lower jaw trays with the actuator-containing band.
Figure 4:
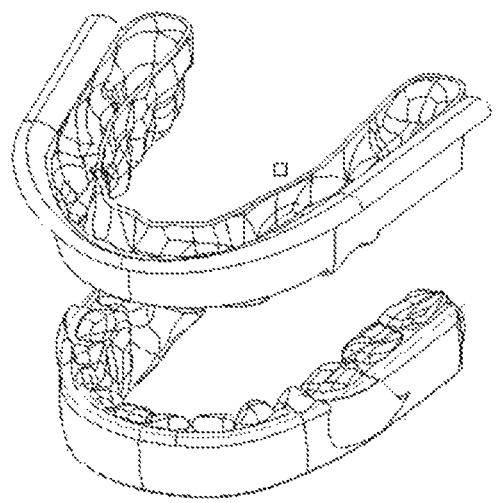
FIG. 4 depicts the upper and lower jaw trays separated from one another.
Figure 5:
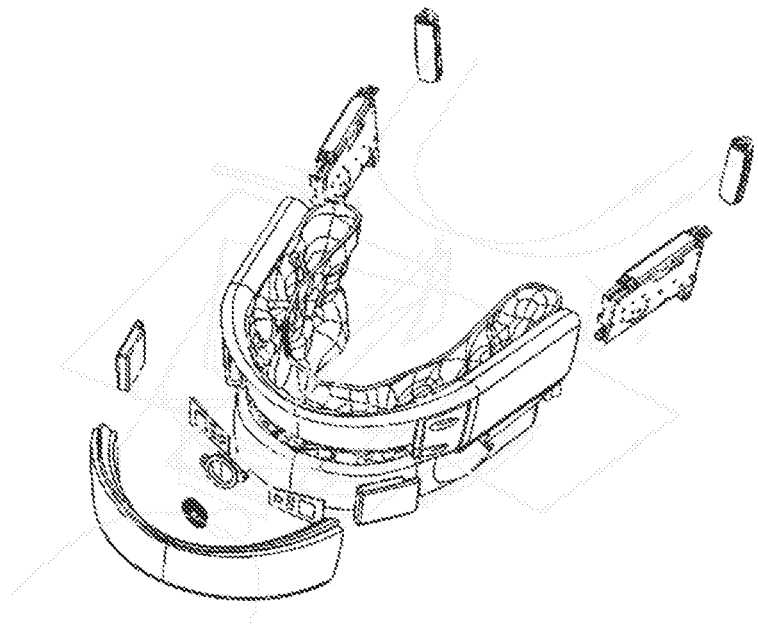
FIG. 5 depicts an exploded view of an embodiment of the invention.
Figure 6:
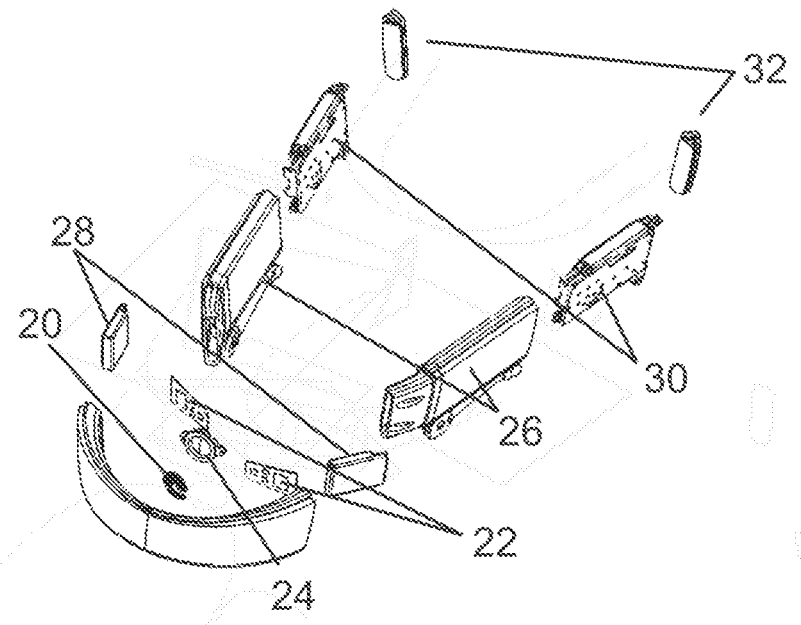
FIG. 6 depicts an exploded view of the actuator-containing band, according to embodiments of the invention.

In some embodiments, a mandibular advancement device for abating sleep disorders may include a maxillary jaw tray configured to fit over the upper teeth of a patient; a mandibular jaw tray configured to fit over the lower teeth of a patient; an electro-mechanical actuator connecting the maxillary and mandibular jaw trays; and/or a microcontroller in communication with at least one sensor, the microcontroller configured to, in response to the occurrence of a predetermined event, send a signal to the actuator indicating that the mandibular jaw tray should extend. In some embodiments, the event is a physiological event. In some embodiments, the event is based upon time.

In some embodiments, the actuator may further include a cart that moves linearly in response to the expansion or contraction of a nitinol wire assembly, or the actuator may include a protruding arm configured to ratchet a ratchet gear with each actuation.

In some embodiments, the actuator is further configured to collect data related to the usage of the device and condition of the patient. In some embodiments, the data may include, one of: total duration of use, frequency of use, number of actuations, and/or number of physiological events.

In some embodiments, the microcontroller and power supply are protected from liquid using a biocompatible polymer or elastomer.

In some embodiments a method of manufacturing and using the aforementioned mandibular advancement device is disclosed, further comprising: providing the mandibular advancement device to a patient; receiving data from the microcontroller relative to the patient's sleep patterns; and transmitting data to the microcontroller to implement a treatment profile.

DETAILED DESCRIPTION

The present invention relates generally to dental appliances, and more specifically to oral devices for the treatment of obstructive sleep apnea, snoring and similar disorders.

Prior devices that advanced the lower jaw or mandible in an outward position prior to sleep have been known to cause discomfort to the wearer, which can lead to a lack of patient compliance with a prescribed device-based treatment regimen.

It has been found that compliance with existing sleep apnea treatment regimens—such as those involving elevated airway pressures (CPAP, APAP and BiPAP), or treatment by MAD dental appliances—suffer from patient compliance issues wherein the patient will discontinue the therapy if the therapy is for instance, not comfortable or is inconvenient or difficult to use. It is therefore a primary objective of the invention described here to improve both patient comfort and by extension, patient compliance with the treatment regime.

In embodiments of the invention, a mandibular advancement device ("MAD") is provided in which the lower (mandibular) tray of the MAD is not advanced until the patient is asleep and begins snoring. The device may also have integral processor based intelligence which allows it to track its own use as well as being able to track patient compliance and device efficacy (as measured by tracking snoring events during device use) and report the compliance and efficacy—via the use of external software—to the sleep physicians and other health care providers overseeing the treatment regimen.

The first function of the invention mentioned, namely, mechanical advancement of the lower jaw tray of the MAD when snoring is detected may be accomplished by two primary components of the invention, namely, upper (maxillary) and lower (mandibular) jaw trays, and an electro-mechanical movement/actuator.

In embodiments, an upper (maxillary) and lower (mandibular) jaw trays may be customized to precisely fit over the teeth of the patient. These trays may be coupled to one another by mechanical means ensuring that their position relative to each other is mechanically controlled. An electro-mechanical movement/actuator may be attached to, hinged to, or mechanically affixed to, the lower (mandibular) and upper (maxillary) trays. The electro-mechanical movement may gently push the lower jaw tray forward during sleep at a speed sufficiently slow and with a minimal amount of mechanical noise (e.g. vibration, sudden sharp movement, or clicking) so as to minimize the potential of sensory detection by the sleeping patient, as awakening the patient would be counterproductive. The activation of the electromechanical movement may be driven by electronic detection of snoring events as sensed using an electronic circuit board that includes components to sense that snoring has occurred, such as a microphone or accelerometer and microcontroller.

In embodiments, device usage (compliance) and efficacy may be tracked using integral electronics that detect the snoring events (including background breathing and device movement) in order that the duration, initiation and cessation times of device usage, as well as frequency, severity, and timing of occlusive (snoring) events can be precisely logged. These electronics may also have the ability to download this logged/recorded data to an external device, tablet, PC, or smartphone and the resident software can itself deliver this logged compliance and efficacy data through the cloud or the Internet to a remote physician for evaluation, assessment or records keeping purposes.

The invention will now be described in detail with reference to the included illustrative figures. While the description here covers a particular implementation of the invention, it will be understood that substituting hardware elements to achieve similar goals of extending the lower jaw forward during sleep and relaying compliance and physiologic data remotely to a physician is within the scope of this invention. For instance, some may choose to initiate the movement of the lower jaw forward based on a "user set" timer, this is simply a variant of the invention described here. Further, some may choose to use a simple linear actuating device to move the lower jaw forward without the use of a latch, ratchet or a spring/damper system, this too should also be considered a variant of the invention described here as it simply uses different hardware configurations to achieve the same ends of actuated lower jaw advancement during sleep and such variants in hardware configurations are easily achieved and should be considered within the scope of this invention.

In embodiments, patient comfort may be enhanced by not requiring that the lower jaw be extended forward during the time in which the patient is falling asleep as it would typically be with existing MAD devices. Such current technology typically allows for adjustment of the amount of lower jaw extension, however, this extension is set (fixed) on the device and must be coped with/tolerated by the patient during the period of falling asleep. This lower jaw extension, of course, produces some measure of patient discomfort. Rather than requiring that the lower jaw be extended during the period of falling asleep, embodiments of the invention permit the upper and lower jaws to be in a relaxed and naturally aligned during the period immediately prior to sleep. Once snoring has been detected, the lower jaw may be extended by extending the lower jaw tray in a very slow and mechanically (predominantly) noise free fashion so as not to disturb the sleep of the patient. The patient is allowed, upon waking up, to realign the upper and lower mandibular trays by pulling the lower jaw in using jaw muscle power whereupon it latches in this comfortable position thus allowing the patient to re-fall asleep also in a comfortable jaw position.

In embodiments, patient compliance may be automatically tracked by the onboard electronics for potential viewing by the treating or prescribing physician. This may be achieved through the use of a real time clock accessible to the microcontroller in combination with the microphone or accelerometer. Specifically, the device is able to track snoring activity and also breathing activity and timestamp and store these events in memory. The invention therefore knows by the presence of these sounds both when apneic events occur and also knows the duration of patient use of the device (by monitoring for the existence of background breathing noise present during device use). The former being critical in determining when to deploy forward the lower mandibular tray and the latter being critical in tracking overall patient compliance with the therapy. The information captured by the microcontroller can be used by the prescribing/treating physician to both determine patient compliance with the treatment regimen as well as to quantify the reduction in snoring following deployment of the lower mandibular tray to potentially allow for adjustments in the amount of lower tray extension. All of this information may be relayed from the device to a dedicated analytical software on the physician's computer or tablet or smartphone. The dedicated analytical software provided to the physician and considered part of this invention will allow the physician to perform remote adjustments of the invention including locking in the maximum lower jaw extension dimension and setting the snoring threshold as well as allowing remote adjustments of the invention as the information exchange between the invention and the physician will be two-way. In embodiments, the device may be connected to a network connection (e.g., the Internet) directly, or through the patient's smartphone, computer or tablet. In embodiments, the device may be configured to communicated directly with the physician's computer via the Internet. Such two-way data communications can be also achieved using, for instance, common cloud based two way communications schemes such as Intel's Internet of Things (IoT) communications convention.

In embodiments, the invention provides for unidirectional actuation of the lower jaw, advancing the lower jaw tray forward after snoring is detected. Should the patient awake, the patient can use the strength of his/her jaw muscles to pull the lower jaw tray inward (overpowering and reversing) the mechanical movement back to its undeployed state. For purposes of this disclosure, "undeployed state" refers to a configuration where the upper and lower jaw trays are aligned vertically, and "deployed state" refers to a configuration where the lower jaw tray is advanced fully forward.

In embodiments, the treating physician may set the allowed lower jaw tray deployment distance, and may also set the duration of deployment actuation (e.g. lower jaw tray deploys over the course of 3, 5, 10 minutes etc.). Other physician settable or factory settable elements may include the ability either to set or select the required patient force to overrun the mechanical movement to realign the upper and lower jaw trays upon awakening) as well as the snore event threshold for initiation of lower jaw tray actuation. All of these settings may be implemented by external software available to the physician accessible to the invention or changes could be implemented by substituting in different mechanical components (such as springs). Alternately, the invention could be ordered from the factory with physician requested presets for these parameters described.

In embodiments, advancement of the lower jaw by the integral mechanical movement(s) may be initiated in response to sensed snoring activity. The advancement mechanism and associated activity can be implemented using two distinct strategies which will be referred herein as the preferred embodiment and the alternate embodiment. In the preferred embodiment which will be discussed first (as well as in the alternate embodiment), the lower jaw tray is advanced forward following detection of snoring in a unidirectional manner. With such unidirectional actuation during sleep, the patient can retract the low jaw tray to its aligned position with the upper jaw tray upon wakeup using his/her jaw muscles to override or overpower the electromechanical movement (via the use of an integral override mechanism).

Figure 14:
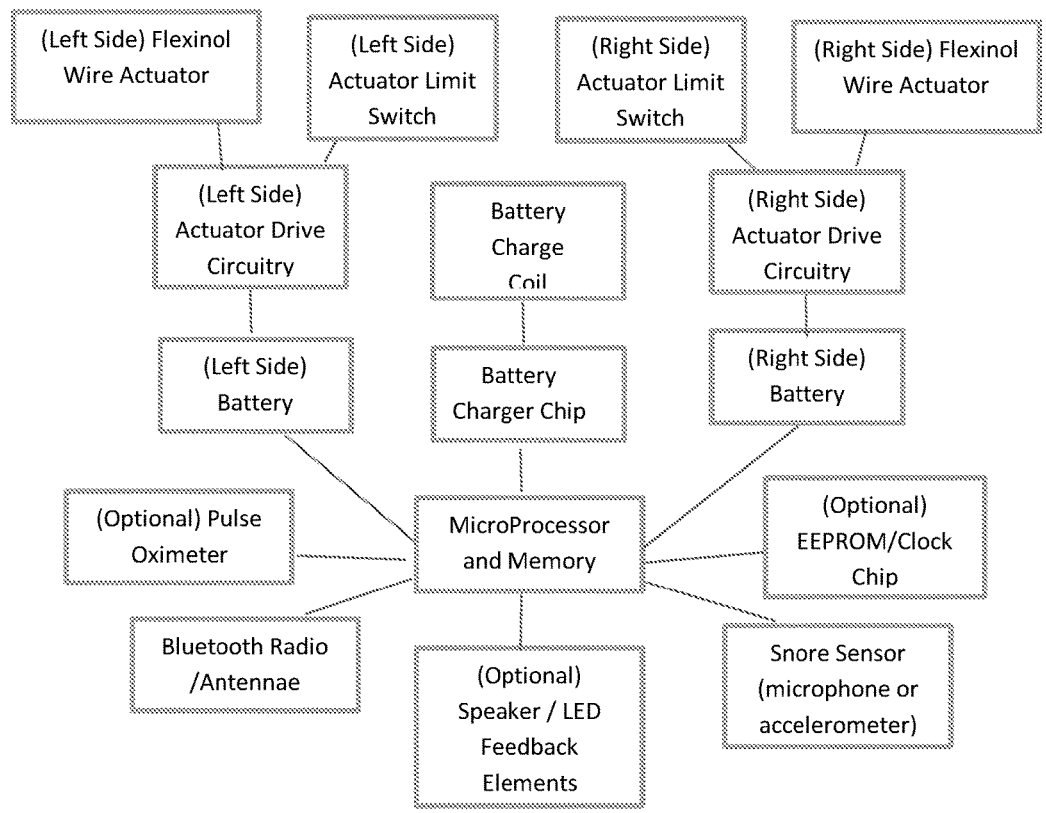
FIG. 14 depicts a block diagram of the major components of the actuation elements of an embodiment of the invention.
Figure 15A:
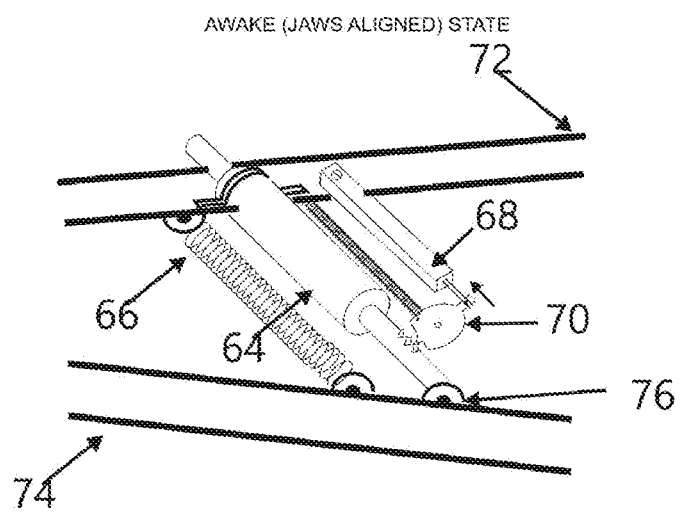
FIGS. 15a-b depict an alternate embodiment for implementing the electromechanical movement of the invention.
Figure 15B:
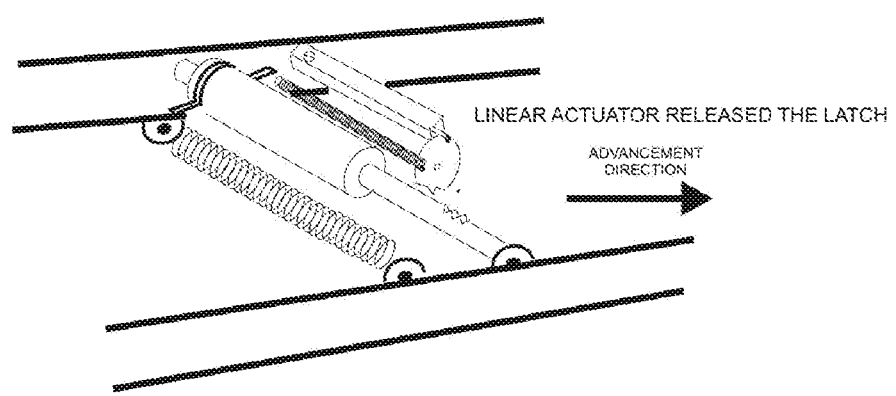

Both actuation techniques described herein employ the same electronics construct and signal processing tasks. A preferred embodiment may contain an electronic circuit board that controls the mirrored actuations on both sides of the jaw tray. The preferred embodiment may place a single microcontroller in command of both actuators with wiring routed through the internals of the actuator housing. The key electronics features may consist of a microcontroller (microprocessor, FPGA or other digital logic processing device) for overall device control, batteries (or large capacitors or super capacitors) for power storage sufficient to last at least one night, an optional wireless charger (or USB based charger) for ease of battery charging, nitinol drive circuitry, an optional RTC clock chip for low power tracking of time of day (for time marking events), an optional Bluetooth or similar wireless communications means for communicating with outside devices such as tablets, PCs or smart phones, an optional EEPROM chip for additional storage of events, a microphone or accelerometer for detection of snoring events, actuator drive circuits, a tone generator for user notification of critical events such as low battery, and optional LED(s). These components are shown graphically in FIG. 14.

In embodiments, a microcontroller system controlling the actuator movement does so by the use of a miniature microphone element that captures sound that is processed by the microcontroller to determine if a snoring event has occurred. Snoring events may be identified by spectral and/or time domain signal processing strategies.

Referring to FIG. 1, in embodiments of the invention, an upper (maxillary) jaw tray 2, lower (mandibular) jaw tray 4, and the actuation band 6 are provided. The actuation band may be attached to the upper jaw tray by a removable interlock connection and itself attaches to the lower jaw tray by the use of two pushrods 8.

Upper and lower jaw trays are preferably created using three-dimensional dental scans of the upper and lower jaw of the patient or, alternatively, created using three-dimensional scans of molded (e.g. plaster replicas) of the upper and lower jaw of the patient jaw anatomy. Such three-dimensional scans may be modified in appropriate programs such as GEOMAGIC STUDIO to thicken the scan surface outwardly producing a three-dimensional solid which represents, on its inner surface, a replica of the scanned surface of the jaw, and on the outer surface, a smoothed projection of the inner surface at some fixed/uniform thickness. In order to achieve this, files from scanned data may need to be converted from one graphics format (such as STL file format) to another format (such as IGES file format) which can be easily manipulated in a CAD environment. The resulting thickened representations of the upper and lower jaw anatomy may then import into a parametric CAD system (such as PTC CREO) for further modification.

Once the upper and lower jaw models are imported into the CAD environment, they may be further parametrically modified to smooth the outer surface of the maxillary tray 10, to add a locking surface to the upper tray for eventual locking of the actuation band 12, and further cosmetic and comfort oriented changes are made to the trays.

The trays may be manufactured using one of two techniques. In the first technique, they may be printed using a three-dimensional printer using biocompatible polymers/resins such as MED610 (Stratasys, Eden Prairie, Minn.). Such materials are available with medical approvals which include cytotoxicity, genotoxicity and delayed hypersensitivity/irritation. Alternatively, the trays may be manufactured using a three-dimensional mold and using this mold to injection mold, investment cast, or thermoform the trays again, using biocompatible polymers. The trays are preferably designed to be thin (e.g., preferably 2 mm or less in thickness) and flexible to optimize patient comfort.

The dental trays may be constructed to be disposable with a limited lifetime which may be dictated by allowed biocompatibility use limits or by hygiene considerations.

In embodiments, the lower tray may include two pockets 14 into which the pushrod mounts. These pockets preferably contain an elevated nub or cylindrical shape which inserts removably to the hole in the pushrod assembly end "eye" element 16 and is held in place by the inside surface of the pocket. The opposite end of the pushrods may be shaped on their inner (actuator contacting surfaces) so as to allow for angular movement relative to the actuator, this coupled with the relative flexibility inherent in the lower dental tray allows overall movement of the lower jaw tray with respect to the upper jaw tray in the following directions up/down (or jaw open/close) and side to side (or jaw side to side displacement). The movement disallowed by the coupling of the pushrods is forward/reverse or advancement/retraction of the lower jaw relative to the upper jaw. In fact, it is on this movement plane that the device operates by moving the lower jaw forward in a controlled manner.

In a preferred embodiment, the actuation band may be constructed to removably lock to the upper jaw tray. The actuation band may consist of a number of subcomponents such as the front portion of the band 18 that houses a coil 20 and two circuit boards 22. The coil may be provided as a component of a wireless charging system integrated into the circuit board which allows a remote docking station (itself containing a coil) to wirelessly charge the invention after use. The coil may be covered by a circular cap 24 which is preferably constructed of (a biocompatible) plastic to facilitate the charging process by not interfering with the electromagnetic nature of wireless charging as for instance a conductive metal cap would. Two side housings of the invention 26 may each plug into the front portion 18 and also house two rechargeable batteries 28 and two actuators 30. Finally, the side housings may be capped on each side 32. The band is designed to be sealed to fluid ingress through the use of O-rings (of biocompatible materials such as silicone) mounted on the caps, the side housings, the circular cap, and other components such as the actuation racks. The actuation band is uniquely fitted to interface coincident with the flat portion of the upper jaw tray and this flat portion is unique in general geometry to each individual patient. Therefore, all elements of the actuation band housing (i.e. the front portion, the side portions and the caps) must be uniquely fitted to the individual patient to ensure that the overall shape of the invention is comfortable to the patient and, for instance, does not protrude excessively outward. Such a unique fitting on a patient-by-patient basis is easily and readily achievable in CAD systems by changing certain elements of the overall design model and regenerating the model to accommodate those changes. Specifically, only small portions of the CAD model will need to be regenerated on a patient-by-patient basis as the unique geometry of both the upper and lower trays as well as the actuation band must be addressed in a cost effective manner during the production phase.

In embodiments, the actuation band may be manufactured using three-dimensional plastic printing techniques (such as stereolithography or fused deposition modeling) using high durometer biocompatible polymers or, alternatively, using a three-dimensional metal printing technique (such as direct metal laser sintering or Selective Laser Sintering) using biocompatible metals such as titanium or cobalt chromium.

Figure 13:
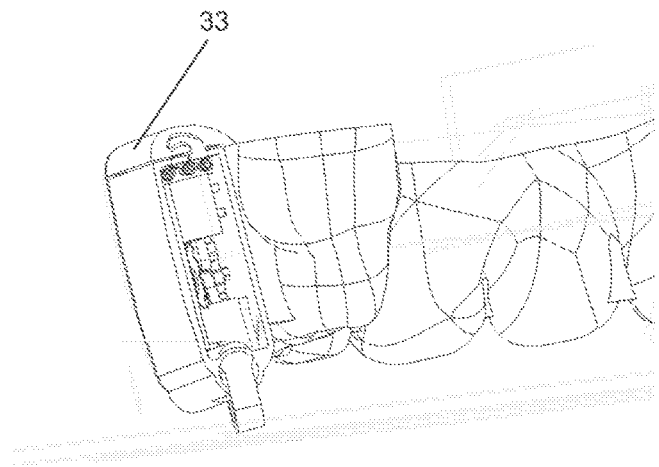
FIG. 13 depicts a close-up of an interlocking seal between an actuator-containing band and the upper jaw tray for use with embodiments of the invention.

The geometry of the interior spaces of the actuation band may allow for the placement of the actuators, batteries and other components which themselves do not change geometry or design on a patient-to-patient basis. This interior geometry consistency can be ensured using the CAD modeling techniques referred to and ensuring that no modeling changes to the interior spaces of the actuation band be made on a patient-by-patient basis. Finally, the actuation band is reversibly locked in place to the upper band using an interlocking geometry approach 33 as shown in FIG. 13.

Two mirrored actuators may be employed to push the lower jaw outward/forward after snoring has been detected. The actuator design is intended to minimize mechanical noise and vibration to the extent where it would be difficult for the patient to sense thus minimizing the chance that the patient will wake during the actuation process. Further, the design is intended to minimize the electrical power required for actuation as minimization of battery size (as well as the size of other components) is critical to keeping the device small and comfortable for the patient. This predominantly silent and energy efficient actuation process is achieved by the use of a nickel titanium (nitinol) alloy based wire called Flexinol (Dyalloy Inc., Irvine, Calif.) wire which reversibly shrinks upon heating/cooling. The heating (shrinking) is achieved by resistive heating of the wire via electrical current flow through the wire. Such nitinol wire is known in the art with nitinol-based designs in medicine common particularly in interventional cardiology products such as stents.

The invention utilizes this reversible shrink property of the nitinol to activate a latch mechanism which in turns both locks the position of the actuator between nitinol actuations and unidirectionally rotates a ratchet gear. The ratchet action ensures that energy is conserved as energy is only used during the actuation process and not used in-between actuations maintaining the actuation position. This ratchet gear is itself connected to a gear train which functions to provide mechanical advantage and to reduce the actuator output displacement to a degree where it will be unnoticeable for the patient. Although many diameters of nitinol wire and gear ratios are possible for such a design, our design which is considered to be advantageous and close to optimal is now discussed.

Figure 8:
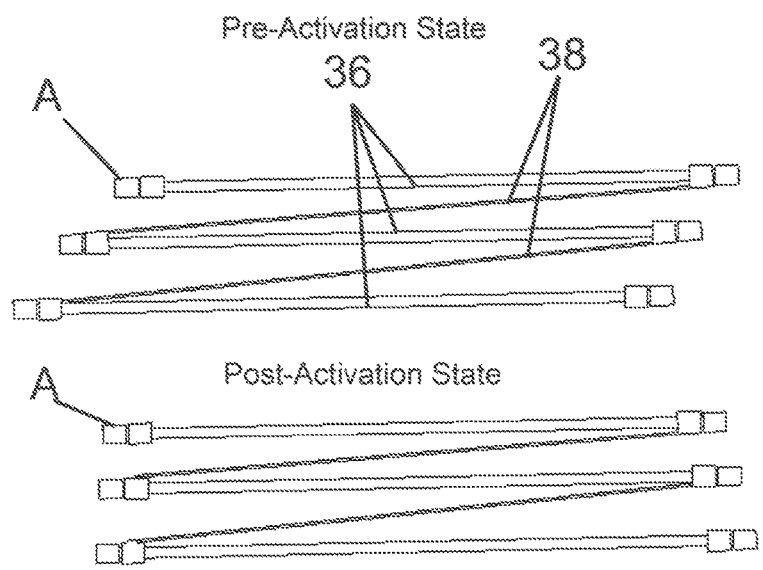
FIGS. 8a and 8b depict a conceptual subset of actuator wire and wire/hypodermic tube sets joined end to end, according to embodiments of the invention.

In embodiments shown in FIGS. 8a and 8B, a nitinol actuator may consist of a bank of nitinol containing hypodermic tubing segments 34 each of which may be re soldered to a traversing nitinol wire at both ends of the tubing segment. These tubing segments 36 may be housed in a non-conductive housing 40 as is the returning (bare) nitinol wire 38. This configuration of a wire housed in the hypodermic tubing and returning bare wire is repeated a number of times in a parallel configuration. Electrical connections ((+)VDC on one side and (−) VDC on the other) may be placed on either side of the overall wire/tubing assembly so that current flows through the entire assembly following the path of the wires and tubes. On the segments in which the wire is housed in the tube and soldered to either end of the tube, the electrical current will flow through the hypodermic tubing instead of the wire as the hypodermic tubing will provide a much reduced resistive path to electrical current flow (and current flows through the path of least resistance). On these hypodermic tubing segments, there will be little if any resistive heating of the wire due to electrical current flow as very little if any current will flow through the wire itself but will instead flow along the walls of the hypodermic tube. On the segments in which the bare wire returns, the current may be routed through the only path available, namely through the wire itself. The current flow through these wire segments produces shrinkage of the wire along the bare segments once enough current has flowed for long enough a period of time to produce resistive heating; approx. 200 mA for 1 second). FIG. 8 shows conceptually the position of a small number of segments pre and post electrical current flow.

The assumption is that the point "A" marked in the figure is statically fixed in place and cannot move. The result is that post-activation, the bottom tube moves to the right by a finite amount which is approximately the displacement imparted by each of the bare wire segments added together. It Is understood that the wire and hypodermic tubing are allowed to slide in the housing which is itself nothing more than a box with integral holes to accommodate the hypodermic tubing and returning wires. The number of tubing segments and diameter and by extension resistivity of the wire should be controlled to meet the design objectives. Design calculations for a close-to-optimized configuration are summarized in the table below for a single actuator and show a need to control a number of factors to ensure adequate force is imparted by the actuator, minimal energy is consumed by the actuator, and minimal mechanical noise is imparted on the patient.

| Design Parameter | Value |
| --- | --- |
| Nitinol Wire Overall Length | 5.4 inches |
| Nitinol Wire Diameter | 0.004 Inch |
| Nitinol Wire Resistivity | 3.2 Ohms/inch |
| Nitinol Wire Overall Resistance | (5.4 inches)*(3.2 ohms/inch) = 17.3 ohms |
| Current Required for Activation | 200 mA |
| Activation Time/Cool off Time | 1 Sec/1 Sec |
| Wire Pull Force | 0.31 lbs pull force minus 0.12 lbs rexation force = 0.19 lbs |
| Anticipated Battery Voltage | Battery is 3.7 Volts, 3.5 Volts anticipated available |
| Current Flow Required for Single Activation | V = IR 3.5 V = I (17.3) I = 202 mA (above 200 mA threshold) |
| Transient Battery Current Flow Requirement | 200 mA flow over 1 second |
| Nitinol Total Displacement per Actuation | 3% = 0.03*5.4 inches = 0.0162" = 4.1 mm |
| Gear Ratio | 10.1:1 note realized gain is approximately 5:1 |
| Rack Movement per Actuator Movement | 0.1 mm (0.004") |
| Actuations Required for 1 cm Movement | 100 actuation |
| Time Required for Actuation of 1 cm | 2 seconds per cycle * 100 actuations = 200 seconds |
| Battery Current per 1 cm Move | 200 mA-sec per actuation *100 = 5.5 mA-Hr |
| Battery Capacity | 40 mA-Hr |

| Design Parameter | Value |
| --- | --- |
| 1 cm Actuations Possible per night | 40 mA-hr/5.5 mA-hr = 7.3 |
| Overall Actuator Pull Force | 0.19 lbs @ 10:1 gain = 1.9 lbs per side or 3.8 lbs total |

Figure 7:
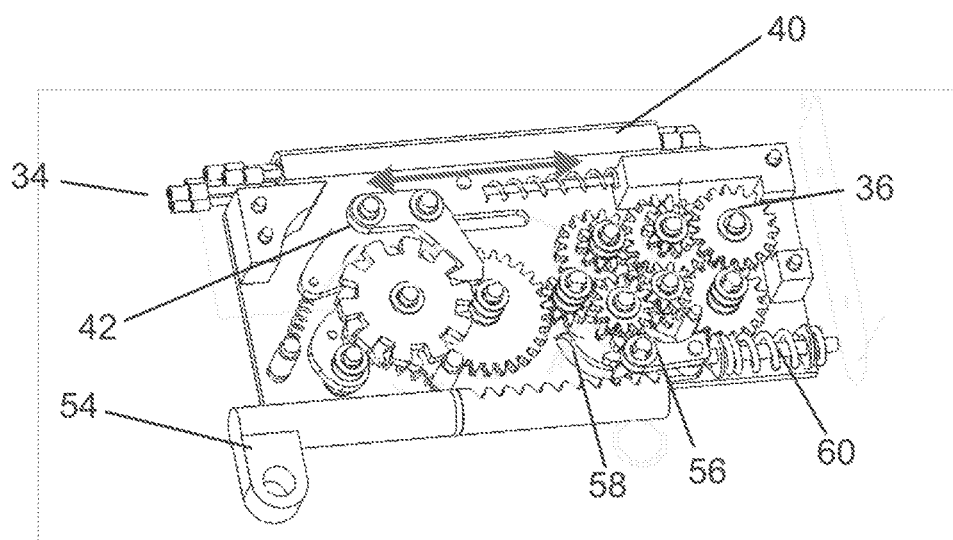
FIG. 7 depicts an actuator with gearing, flexinol-based push rods, and drive rack and pinion components, according to embodiments of the invention.
Figure 9:
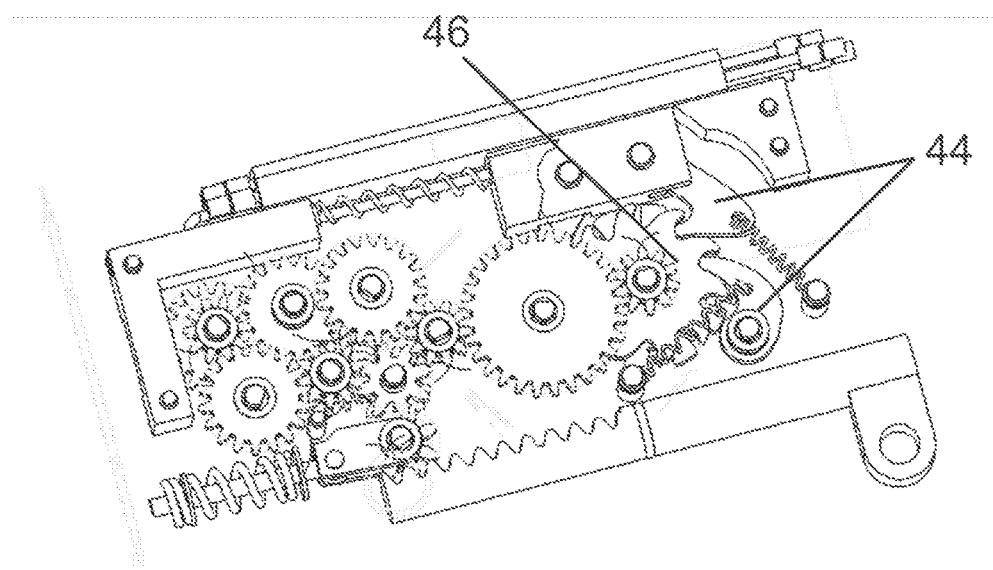
FIG. 9 depicts one side of the actuator with plates removed, according to embodiments of the invention.
Figure 10:
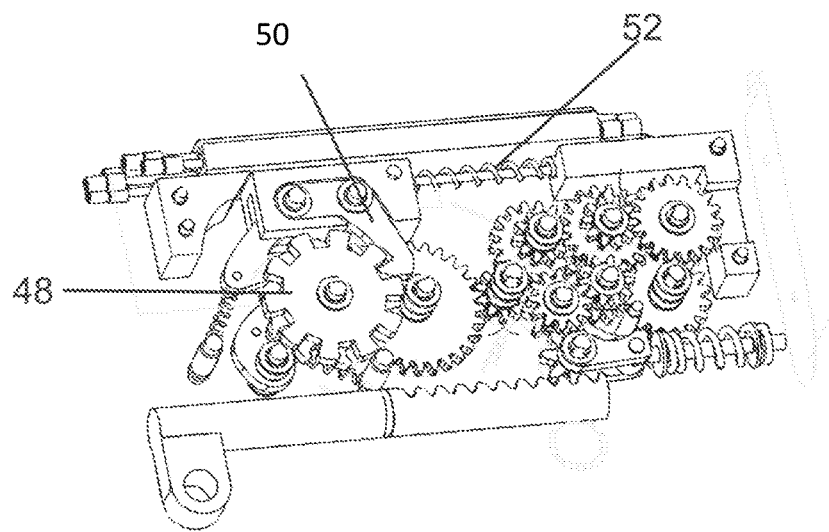
FIG. 10 depicts a second side of the actuator with plates removed, according to embodiments of the invention.
Figure 11:
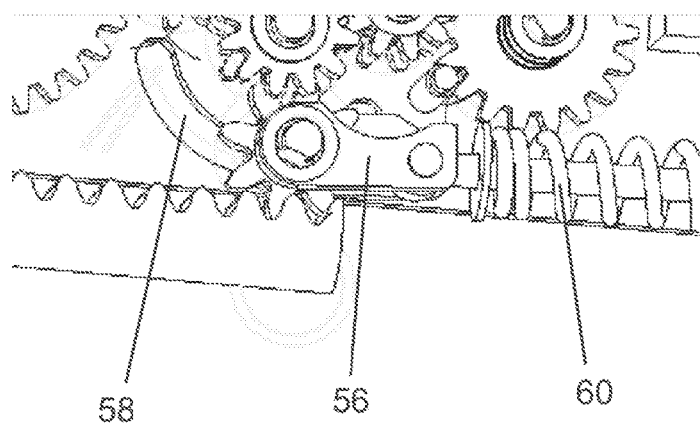
FIG. 11 depicts a close-up of an actuator override mechanism for use with embodiments of the invention.
Figure 12:
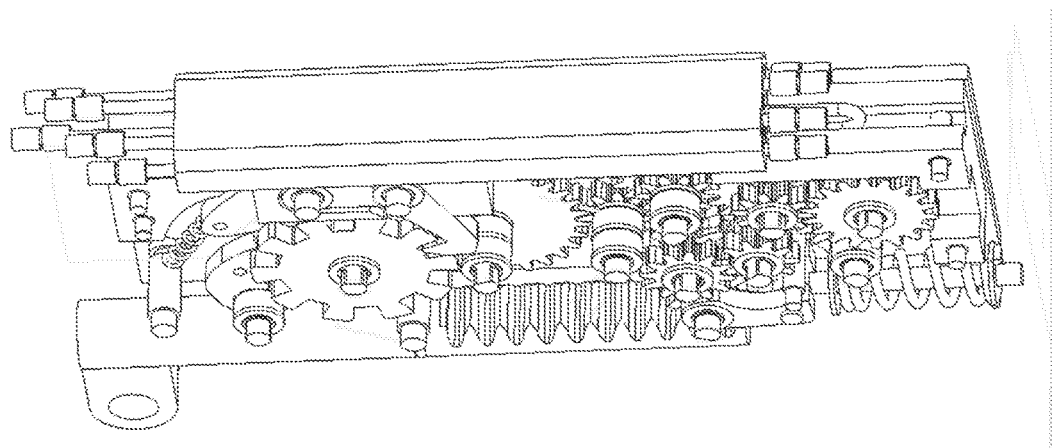
FIG. 12 depicts a close-up of a nitinol (flexinol) rod-based actuation elements for use with embodiments of the invention.

The movement of the nitinol wire segments produce a linear movement which is translated to a cart that can travel back and forth based on nitinol actuator movement as shown by the blue arrow in FIG. 7. This cart may contain three protruding arms, namely, two on one side of the actuator and a third on the opposing side, as shown in FIGS. 9, 10. The arms may consist of two pawls 44 that are spring loaded and configured to circularly ratchet a ratchet gear 46 by one tooth per actuation.

Referring to FIG. 10, the back side of the ratchet gear may contain a square tooth gear 48 on the same axle and the third arm 50 of the cart, namely a locking pawl. This locking pawl can hold the square tooth gear in place between actuations so that movement in both directions is prohibited (note, the ratchet only prevents movement in one direction). Thus, for each nitinol shrink/relax actuation event, the ratchet gear may rotate forward one tooth distance and at the end of the actuation period, the locking pawl engages holding the actuator in place so that external loads cannot rotate the gears.

It should be noted that the movement of the cart is coupled to the movement of the nitinol actuator by a 180-degree "U" segment which attaches both to the last hypodermic tubing segment of the actuator as well as rigidly to the cart.

Lastly, a restoration force may be applied to the nitinol actuator in order to ensure that the nitinol wire returns to its pre-heated length during the cooling process. Such a restoration force is applied by using compression spring 52, which serves to oppose actuator movement during actuation and also produce the restoration force during the wire cooling stage to restore the wire length to its original (pre-heating) length. The required force needed is known in the flexinol specifications and this required force may be easily calculated for the spring using the spring constant of the spring itself in order that the force can be accurately applied to the wire segments.

The advancement of the ratchet gears is preferably angular and intermittent as defined by the shrink/relaxation states of the nitinol actuator. This angular advancement is modified by an attached gear train 36 which performs two functions. First, the gear train 36 reduces the angular displacement of the ratchet gears by an amount equal to the gear ratio of the gear train. Second, it increases, by mechanical advantage, the force imparted by the actuator (as seen at the rack and pinion stage) by an amount equal to the gear ratio of the gear train. The gear ratio should be selected to ensure that adequate force can be generated by the actuator to move the jaw muscles during actuation, bearing in mind that since jaw musculature is relaxed, or atonic during sleep and significantly less force is required to advance the jaw than would be required of an awake patient.

In addition, the gear ratio should be selected so as to minimize the amount of movement of the actuator and by extension lower jaw during actuation so as not to awaken the patient due to the sensation of movement of the lower jaw.

Finally, the gear ratio should be selected so as to minimize power consumption and provide acceptable battery life. Very small movements may require more actuations and thus more power, unnecessarily reducing the battery life of the device. Thus, the selection of the optimal gear ratio is a matter of optimization. The above table shows a preferred gear ratio.

Gears in this gear train (with the exception of the ratchet gears and rack and pinion gears) are so-called involute gears which produce a smooth tooth to tooth contact and smooth or low noise actuation of the gear train. The final portion of the actuator consists of a rack and pinion 54 stage with an integral override mechanism 56. The rack and pinion stage serves to translate angular movement of the gears to linear movement. The rack is then attached to the pushrods which attach to the lower jaw tray. The design of the rack and pinion includes the provision of override functionality. Override functionality allows the patient to, upon wakeup, re-align the upper and lower jaws for comfort. This is achieved by having the patient impart a significant force on the jaw trays using the jaw musculature to override or over power the actuator assembly. This is achieved mechanically by having the pinion gear ride in a circular track 58 and held in place laterally by a spring assembly which functions to hold the pinion gear centrally and in contact with the rack. The spring assembly requires force to move it in either direction and this force would originate from the patient jaw musculature. Once a large lateral load is imposed on the rack and pinion spring assembly by the patient, the spring either compresses or extends (depending on the direction of force) and this causes the pinion gear to follow the curved track which ultimately, if the force is adequate, will cause the pinion gear to lose contact with the rack thereby allowing the rack to "slip" in the direction of imposed force.

The override mechanism may serve two functions. First, it protects the internal gearing and in particular the potentially fragile pawls from becoming overloaded and bending or breaking. Second, the override mechanism can allow the patient to reset the device to a comfortable position in which the upper and lower jaw are aligned upon wakeup thus allowing the patient to return comfortably to sleep. The internal electronics will note this movement (by noting the change of state of an internal limit switch) and reset the actuation functionality of the actuator to resume unidirectional actuation upon further detection of snoring activity.

The mechanical components within the actuator are preferably small to ensure that the device is small for optimized patient comfort. The gears themselves can be constructed by a number of techniques including wire electrical discharge machining (EDM), laser cutting, stamping, fineblanking, metal injection molding, and metal sintering. The small gear axles and the rack can be constructed using machining such as Swiss screw machines for precision parts fabrication. Finally, the plates that sandwich in the gears can be constructed also using stamping, EDM and laser cutting techniques. The housing that captures the nitinol wires and hypodermic tubing of the nitinol actuator can be constructed using laser cutting techniques, can be designed in layers and glued or ultrasonically welded together during fabrication of the nitinol actuator, and can be constructed of high temperature plastics (such as PEEK-HT) with laser cut holes that will allow the in situ soldering of the hypodermic tubing to the nitinol without the risk of melting the housing.

FIG. 13 shows the components both essential and optional for the microcontroller based electronics board. An electronics board may be embedded in the upper or lower jaw tray, and is preferably positioned on the same side of the teeth as the electro-mechanical movements and preferably next to or co-housed with the movements. The battery may be rechargeable, e.g., lithium ion, and is housed in a likewise liquid ingress protected housing.

The electronics board drives movements on either side of the mouth and may do so by wires or flex circuits embedded in the upper or lower jaw trays and traversing the tray through the front portion of the housing to reach both movements while likewise being protected from liquid ingress. The electronics circuit board preferably comprises small surface-mount components.

The circuit board may include a sensor—such as a microphone or accelerometer—that can detect snoring. The gain of any microphone amplification stage before the introduction of the signal to the microcontroller should be adjusted to optimally function through any water ingress protection for the circuit board that may attenuate the sound or vibration signal.

A microcontroller (which can be replaced by an FPGA or similar digital logic processing device) should have sufficient speed and memory to process the snoring sounds and may optionally include either battery-backed RAM, flash memory, or EEPROM to store data on compliance or use for later retrieval.

The battery may be included in the electronics as is the charge maintenance chips necessary to oversee battery charge maintenance and the coil required for wireless charging from an external docking station. A real-time clock (RTC) chip may be provided for low-current time of day tracking so that all microcontroller time stamped events such as snoring events can be properly tagged with the correct time of day.

Limit switches in each actuator may be provided to signal the limits of movement of the actuator and nitinol drive circuits are also included to provide an adequate and microcontroller timed current source to the nitinol wires. This current supply can be supplied in an on/off fashion as is associate with FET type drivers or this current supply can be provided in a pulse width modulated scheme to provide somewhat time averaged sinusoidal drive current to the wires based on the timing of the on/off sequences to reduce the noise from and thermal shock to the nitinol wires.

External software may be provided to enable a treating physician to monitor the patient's progress and the status of the device.

Lastly, a number of optional elements may be added to the electronics circuit board such as an LED or audible signal generator to provide feedback to the patient on, for instance, whether the upper and lower jaw realignment (or reloading) was done successfully or whether the device is fully charged. Alternatively, Bluetooth or other wireless transceivers may be incorporated to facilitate the data exchange with external devices by wirelessly accessing these devices.

In addition to monitoring snoring and deployment of the lower mandibular tray, the electronic circuit board may track snoring events as well as tracking patient usage of the device using timers in sync with sensing of snoring events to determine when the invention is being worn by the patient for device power up needs. Such snoring activity during device use and time and duration of device use is stored in the memory of the microcontroller.

In addition to the electronic circuit board components mentioned, a wireless charging means may be provided for the circuit board to allow the device to be placed on a wireless charger or docking station to charge when not in use. This feature may be implemented using a wireless charging chips and such chips are well known in the art as well as using the previously described integral coil.

This information may be downloadable to external software or delivered to a treating physician by a secure network connection. The physician may then assess the patient's sleep patterns and make modifications to the treatment regimen as necessary.

Various optional components may be utilized to extend the functionality of the device. For example, an audible tone generator may be used to alert the user during times of dangerous snoring or apneic events. A physician in communication with the device may be enabled to define the parameters for such warnings. Alternatively, a component such as the such as the MAX30102 solid state pulse oximeter from (Maxim Integrated of San Jose, Calif., could be integrated to track and timestamp the level of oxygen in the blood, and monitor heartrate. This additional data may provide further insight into a patient's condition during sleep and enhance evaluation of the patient.

FIGS. 17a-d show the signal processing tasks required for detecting snoring events. The microcontroller performs signal processing on the incoming sound or movement data from the microphone or accelerometer to determine if snoring is occurring.

In embodiments, a raw or hardware-filtered signal 106 is collected and then digitally filtered to isolate signal band characteristics associated with snoring activity 108. The signal is then rectified and smoothed using a low pass filter technique 110, which results in a signal whose amplitude is reflective of the strength of the snoring event. The signal is then integrated to obtain a running collection of snoring event signal strengths 112. Once the signal exceeds a preset snoring threshold, the latch is directed to open by the processor and the integral is reset to zero.

Other techniques may also be used to determine the strength of the snoring as a precursor to latch operation such as taking the Fourier transform of the raw signal and analyzing the signal strength in the band of interest as a means to determine whether to activate the latch. Other techniques known in the art include linear predictive coding and wavelet analysis which can also be used for identifying snoring events.

Figure 16:
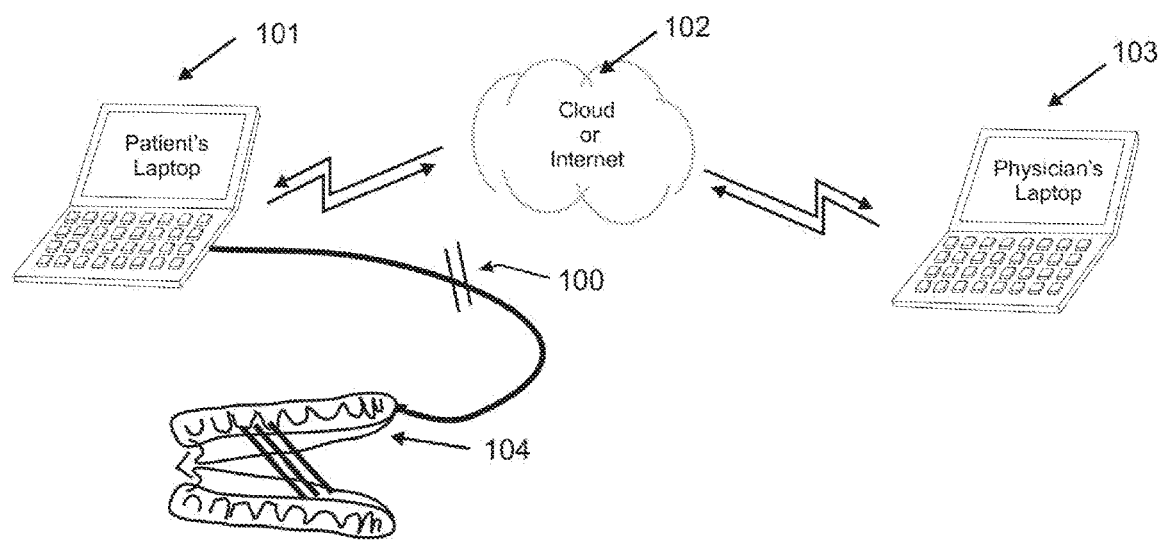
FIG. 16 depicts a two-way communications method between an embodiment of the invention and the physician's computer.
Figure 17A:
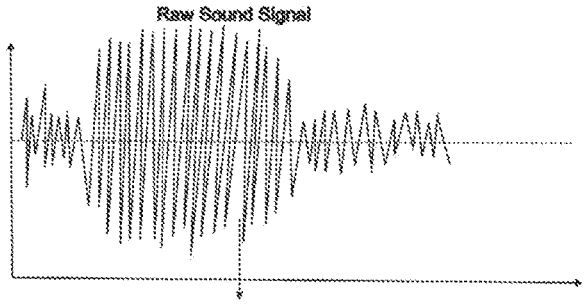
FIGS. 17a-d depict a method of signal processing to identify snoring events.
Figure 17B:
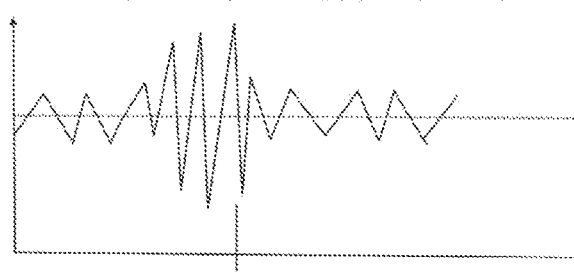
Figure 17C:
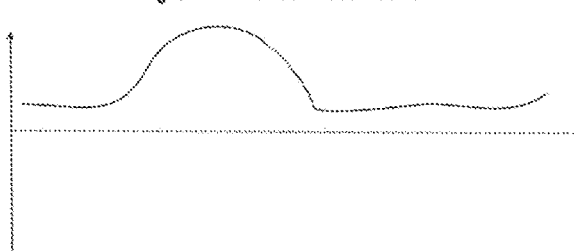
Figure 17D:
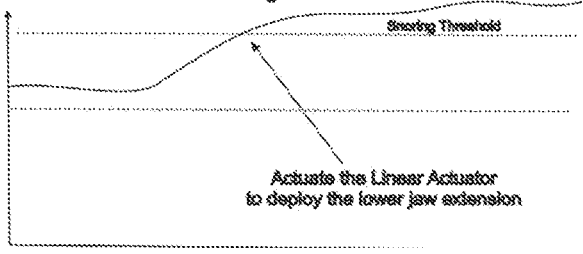

FIG. 16 shows an exemplary connection framework for use with embodiments of the invention. The device 104 may be connected—wirelessly or by wire—to a laptop, smart phone or tablet of the patient 101. Data from device 104 may be downloaded or transmitted through the Internet or the cloud 102 to the physician's laptop, smart phone or tablet 103. It should be noted that information exchange is preferably two-way allowing the physician to not only monitor device function, snoring improvement, and compliance data but also to command remotely performance aspects of the invention such as resetting the allowed amount of jaw forward movement on the device. Such physician requests may be implemented on the invention or may require patient adjustment of the device manually after receipt of the physician's commands through the digital connection.

In embodiments, the unidirectional actuators of the device have a control system consisting of a state machine that monitors a threshold Boolean code that changes state in response to snoring exceeding a predefined threshold. One the threshold is exceeded, the control system may command repeated ratchet activations of the nitinol wire actuator until an integral limit switch (integral in each actuator) indicates that the predefined limit of lower jaw extension has been reached. Once this occurs, the control system is deactivated until such time as the limit switch indicates that either: (a)

the actuator is no longer indicating the actuator is at its predefined limit or (b) snoring has again exceed a threshold value.

In an alternate embodiment of the invention, a damper mechanism 64 which consists of a cylinder piston assembly filled with a highly viscous yet somewhat uncompressible and bio-inert fluid such as vegetable oil. The piston head would have a number of small holes and at least one larger hole (laser cut) in it to allow the movement of fluid from one side of the piston to the other thus allowing for piston movement. The small holes would serve to allow fluid movement during forward deployment of the lower jaw assembly and the diameter and number of holes would control deployment speed. The larger hole(s) would be covered with a die or laser cut flap valve which would open upon retraction of the lower jaw by the patient upon wakeup allowing for speedy movement of the electromechanical movement back to its loaded (upper and lower jaw tray aligned) state. The flap valve, conversely would close over the larger hole(s) during forward deployment of the electro-mechanical movement thus ensuring a very slow deployment consistent with not waking the patient up. Finally, a small amount of compressible microporous closed cell media such as a circular piece of die cut microporous closed cell rubber or foam would be inserted into the compression chamber of the cylinder. This media allows for pressure equalization of the non-compressible fluid media during forward and reverse stroking of the piston which can be adversely affected by the additional volume imposed by the cylinder rod during the stroke. Such methods of pressure equalization are achieved in, for instance, shock absorbers by the use of tube-in-tube arrangements for oil movement or by the use of single tube arrangements with an air filled chamber within the single compression chamber. In the case of this invention, neither of those solutions are easily implemented due to the small size of the cylinder so the compressible microporous closed cell media will serve the purpose of ensuring accommodation of volume disparities owing to the volume occupied by the cylinder rod.

A spring element 66 of the electromechanical movement may consist of a spring either mounted coaxial with the damper (as in an automotive "coil over" arrangement or may be be mounted side by side with the damper. The spring constant would be adjusted for optimal advancement and retraction force suitable to the patient or patient population.

A latch mechanism 68 may consist of a spring-loaded latch 70 that is controlled by nitinol (e.g. flexinol or muscle wire and as a substitute electroactive polymer may be used) actuation (under microcontroller control). Other methods of actuation such as solenoids or a miniature DC motor can be utilized, but as with the other nitinol-based movements described here, nitinol provides a silent and volumetrically efficient linear actuation means for, in this case, latch disengagement when the patient is asleep. The latch may be further implemented so as to have an auditory snap upon reseating of the spring-damper system in the loaded or undeployed position so that when the patient uses his jaw muscle to realign the upper and lower jaw trays upon wakeup this snapping sound is evident, signifying to the patient that the electromechanical movement is loaded. As with the preferred embodiment, all mouth fluid contacting surfaces preferably consist of bio-inert or biocompatible materials and physician or factory adjustment of the performance parameters are available. The mechanism proper is attached to the upper jaw tray 72 and lower jaw tray 74 by the use of mechanical pins 76 which allow for rotation of the mechanism relative to the upper and lower jaw trays.

It will be understood that there are numerous modifications of the illustrated embodiments described above which will be readily apparent to one skilled in the art, including any combinations of features disclosed herein that are individually disclosed or claimed herein, explicitly including additional combinations of such features. These modifications and/or combinations fall within the art to which this invention relates and are intended to be within the scope of the claims, which follow. It is noted, as is conventional, the use of a singular element in a claim is intended to cover one or more of such an element.

I claim:

1. A mandibular advancement device for abating sleep disorders, comprising:
   a maxillary jaw tray configured to fit over a plurality of upper teeth of a patient;
   a mandibular jaw tray configured to fit over a plurality of lower teeth of a patient;
   an electro-mechanical actuator connecting said maxillary and mandibular jaw trays; and comprising a cart that moves linearly in response to the expansion or contraction of a nitinol wire assembly, and a protruding arm configured to ratchet a ratchet gear with each actuation; and
   a microcontroller in communication with at least one sensor, said microcontroller configured to, in response to an occurrence of a predetermined event, send a signal to an actuator indicating that the mandibular jaw tray should extend.

2. A method for treatment of sleep disorders comprising:
   manufacturing a mandibular advancement device by: (a) generating a three-dimensional profile of a patient's upper and lower teeth; (b) creating maxillary and mandibular jaw trays based upon said profile, and connecting said maxillary and mandibular jaw trays with an actuator whose movement is based on the expansion or contraction of a wire assembly, and comprises a protruding arm configured to ratchet a ratchet gear with each actuation; (c) providing a microcontroller in communication with at least one sensor, said microcontroller configured to, in response to the occurrence of a predetermined event, send a signal to said actuator indicating that the mandibular jaw tray should extend;
   providing said mandibular advancement device to a patient;
   receiving data from said microcontroller relative to the patient's sleep patterns; and
   transmitting data to said microcontroller to implement a treatment profile.

3. The method of claim 2 wherein said actuator further comprises biocompatible polymer or elastomer for protecting said microcontroller.

4. The method of claim 2 wherein said data includes one of: total duration of use, frequency of use, number of actuations, and number of physiological events.

5. A device for treating sleep disorders comprising:
   a maxillary jaw tray configured to fit over the upper teeth of a patient;
   a mandibular jaw tray configured to fit over the lower teeth of a patient;
   actuator for connecting said maxillary and mandibular jaw trays, said actuator comprising a cart that moves linearly in response to the expansion or contraction of a nitinol wire assembly, and a protruding arm configured to ratchet great with each actuation; and means for detecting a predetermined event and directing said actuator means to extend the mandibular jaw tray.

\* \* \* \* \*